United States Patent
Swedlow et al.

(10) Patent No.: US 6,463,310 B1
(45) Date of Patent: Oct. 8, 2002

(54) METHOD AND CIRCUIT FOR STORING AND PROVIDING HISTORICAL PHYSIOLOGICAL DATA

(75) Inventors: David B. Swedlow, Danville; Stephen L. Daleo, Dublin; Thomas J. Yorkey, San Ramon; Edward M. Richards, Pleasanton; Charles Porges, Orlinda; Charles Stuart, San Jose; Daniel M. Nemits, San Francisco; Russell L. Delonzor, San Ramon, all of CA (US)

(73) Assignee: Mallinckrodt, Inc., Hazelwood, MO (US)

(*) Notice: Subject to any disclaimer, the term of this patent is extended or adjusted under 35 U.S.C. 154(b) by 0 days.

(21) Appl. No.: 09/520,104

(22) Filed: Mar. 7, 2000

Related U.S. Application Data

(60) Provisional application No. 60/123,266, filed on Mar. 8, 1999.

(51) Int. Cl.[7] ............................................. A61B 5/00
(52) U.S. Cl. ........................ 600/323; 600/322; 600/331
(58) Field of Search ........................ 600/309–311, 316, 600/326, 322–324, 331, 336, 300–301; 356/39, 41; 359/39–42; 128/903, 904, 920

(56) References Cited

U.S. PATENT DOCUMENTS

| | | | | |
|---|---|---|---|---|
| 4,053,951 A | * | 10/1977 | Hudspeth et al. | 600/301 |
| 4,827,943 A | * | 5/1989 | Bornn et al. | 600/481 |
| 4,858,615 A | | 8/1989 | Meinema | |
| 5,490,516 A | * | 2/1996 | Hutson | 600/508 |
| 5,507,288 A | * | 4/1996 | Bocker et al. | 600/322 |
| 5,645,059 A | | 7/1997 | Fein et al. | |
| 5,758,644 A | * | 6/1998 | Diab et al. | 600/323 |
| 5,987,343 A | * | 11/1999 | Kinast | 600/323 |
| 6,125,296 A | * | 9/2000 | Hubelbank | 600/573 |
| 6,200,265 B1 | * | 3/2001 | Walsh et al. | 670/300 |

* cited by examiner

Primary Examiner—Eric F. Winakur
Assistant Examiner—Matthew Kremer
(74) Attorney, Agent, or Firm—Townsend & Townsend & Crew LLP

(57) ABSTRACT

A mechanism for storing and providing historical physiological data, such as blood oxygen saturation data, for a patient. In particular, the historical physiological data is stored in a storage medium that "travels" with the patient and is accessible wherever the patient is moved. This is achieved by storing the physiological data within a sensor assembly. At the destination site, a monitor or a device capable of interfacing with the sensor electronics can retrieve and display the data. The historical physiological data allows a clinician or medical personnel at the destination site to assess the condition of the patient for the entire time that the patient has been monitored. Various types of physiological data can be stored including, but not limited to, blood oxygen saturation, heart rate, and temperature data. Compression of the data can be performed to enhance the storage capability.

20 Claims, 2 Drawing Sheets

METHOD AND CIRCUIT FOR STORING AND PROVIDING HISTORICAL PHYSIOLOGICAL DATA

This application claims the benefit of U.S. Provisional Application Serial No. 60/123,266, filed Mar. 8, 1999, which is incorporated herein by reference.

BACKGROUND OF THE INVENTION

The present invention relates to physiological monitoring instruments and, in particular, sensors that include a mechanism for storing and providing to a monitor historical physiological data such as blood oxygen saturation data.

Pulse oximetry is typically used to measure various blood flow characteristics including, but not limited to, the blood oxygen saturation of hemoglobin in arterial blood and the rate of blood pulsation corresponding to each heartbeat of a patient. Measurement of these characteristics has been accomplished by the use of a non-invasive sensor that passes light through a portion of a patient's blood perfused tissue and photo-electrically senses the absorption and scattering of light in such tissue. The amount of light absorbed is then used to estimate the amount of blood constituent in the tissue. The "pulse" in pulse oximetry comes from the time varying amount of arterial blood in the tissue during the cardiac cycle. The signal processed from the sensed optical signal is a familiar plethysmographic waveform due to cycling light attenuation.

To estimate blood oxygen saturation of a patient, conventional two-wavelength pulse oximeters emit light from two light emitting diodes (LEDs) into a pulsatile tissue bed and collect the transmitted light with a photodiode (or photo-detector) positioned on an opposite surface (i.e., for transmission pulse oximetry) or an adjacent surface (i.e., for reflectance pulse oximetry). One of the two LEDs' primary wavelength is selected at a point in the electromagnetic spectrum where the absorption of oxyhemoglobin ($HbO_2$) differs from the absorption of reduced hemoglobin (Hb). The second of the two LEDs' wavelength is selected at a different point in the spectrum where the absorption of Hb and Hb $O_2$ differs from those at the first wavelength. Commercial pulse oximeters typically utilize one wavelength in the near red part of the visible spectrum near 660 nanometers (nm) and one in the near infrared (IR) part of the spectrum in the range of 880–940 nm.

Oxygen saturation can be estimated using various techniques. In one common technique, the photo-current generated by the photo-detector is conditioned and processed to determnine the modulation ratio of the red to infrared signals. This modulation ratio has been observed to correlate well to arterial oxygen saturation. The pulse oximeters and sensors are empirically calibrated by measuring the modulation ratio over a range of in vivo measured arterial oxygen saturations ($SaO_2$) on a set of patients, healthy volunteers, or animals. The observed correlation is used in an inverse manner to estimate blood oxygen saturation ($SpO_2$) based on the measured value of modulation ratios of a patient. The estimation of oxygen saturation using modulation ratios is described in U.S. Pat. No. 5,853,364, entitled "METHOD AND APPARATUS FOR ESTIMATING PHYSIOLOGICAL PARAMETERS USING MODEL-BASED ADAPTIVE FILTERING", issued Dec. 29,1998, and U.S. Pat. No. 4,911,167, entitled "METHOD AND APPARATUS FOR DETECTING OPTICAL PULSES", issued Mar. 27, 1990. The relationship between oxygen saturation and modulation ratio is further described in U.S. Pat. No. 5,645,059, entitled "MEDICAL SENSOR WITH MODULATED ENCODING SCHEME," issued Jul. 8, 1997. All three patents are assigned to the assignee of the present invention and incorporated herein by reference.

The LEDs and photo-detector are typically housed in a reusable or disposable oximeter sensor that couples to the pulse oximeter electronics and the display unit (hereinafter referred to as the monitor). The sensors are often connected to patients for long periods of time. Conventionally, historical physiological data for the patient is collected, if at all, by the monitor coupled to the sensor. The historical data can be valuable to a clinician or medical personnel for diagnostic and monitoring purposes.

Patients are often moved to various locations during treatment. For example, a patient may be picked up in an ambulance, delivered to an emergency room, moved to an operating room, transferred to a surgical recovery room, transferred to an intensive care unit, and then moved to a nursing floor or other locations. Thus, the patient may be moved between various locations within the same hospital, or between different hospitals. In many instances, the sensor employed to monitor the condition of the patient is adhesive in its attachment and remains with the patient. The monitors, however, are typically local to particular locations within a facility or vehicle. The sensor is normally disconnected from the monitor at a departure site and reconnected to another monitor at a destination site. Consequently, any historical physiological data collected by the monitor at the departure site is normally unavailable to the clinician attending the patient at the destination site.

Accordingly, it is highly desirable to provide mechanisms for storing and providing historical physiological data that travels with a patient independent of any monitor which has previously been connected to the patient.

SUMMARY OF THE INVENTION

The invention provides a mechanism for storing and providing historical physiological data, such as blood oxygen saturation data, for a patient. In particular, the historical physiological data is stored in a storage medium that "travels" with the patient and is accessible wherever the patient is moved. This is achieved by storing the physiological data within a sensor assembly, e.g., sensor itself, connector plug, connector cable, or interconnection module. At the destination site, a monitor or a device capable of interfacing with the sensor assembly electronics can retrieve and display the data. The historical physiological data allows a clinician or medical personnel at the destination site to assess the condition of the patient for the entire time that the patient has been previously monitored. The invention can be used to store and provide various types of physiological data including, but not limited to, blood oxygen saturation, heart rate, blood pressure, and temperature data.

A specific embodiment of the invention provides a pulse oximeter sensor that includes a number of light sources, at least one photo-detector, and a memory circuit associated with the sensor. The light sources are selected to operate at different wavelengths. The photo-detector receives light emitted by the plurality of light sources. The memory circuit stores physiological data derived from the detected light and sent to the circuit by an oximeter monitor, and the circuit then provides the data later when requested by a monitor. The physiological data is indicative of a physiological condition of a patient being monitored by the sensor.

Another specific embodiment of the invention provides a method for storing physiological data. The method detects, via a sensor, at least one signal indicative of a physiological condition, and conditions the detected signal to generate data samples. The data samples are processed to generate the physiological data, wherein the physiological data describes the physiological condition. The physiological data is stored within a memory associated with the sensor. The physiological data can be coded and compressed before storage to the memory.

The foregoing, together with other aspects of this invention, will become more apparent when referring to the following specification, claims, and accompanying drawings.

DESCRIPTION OF THE SPECIFIC EMBODIMENTS

Figure 1:
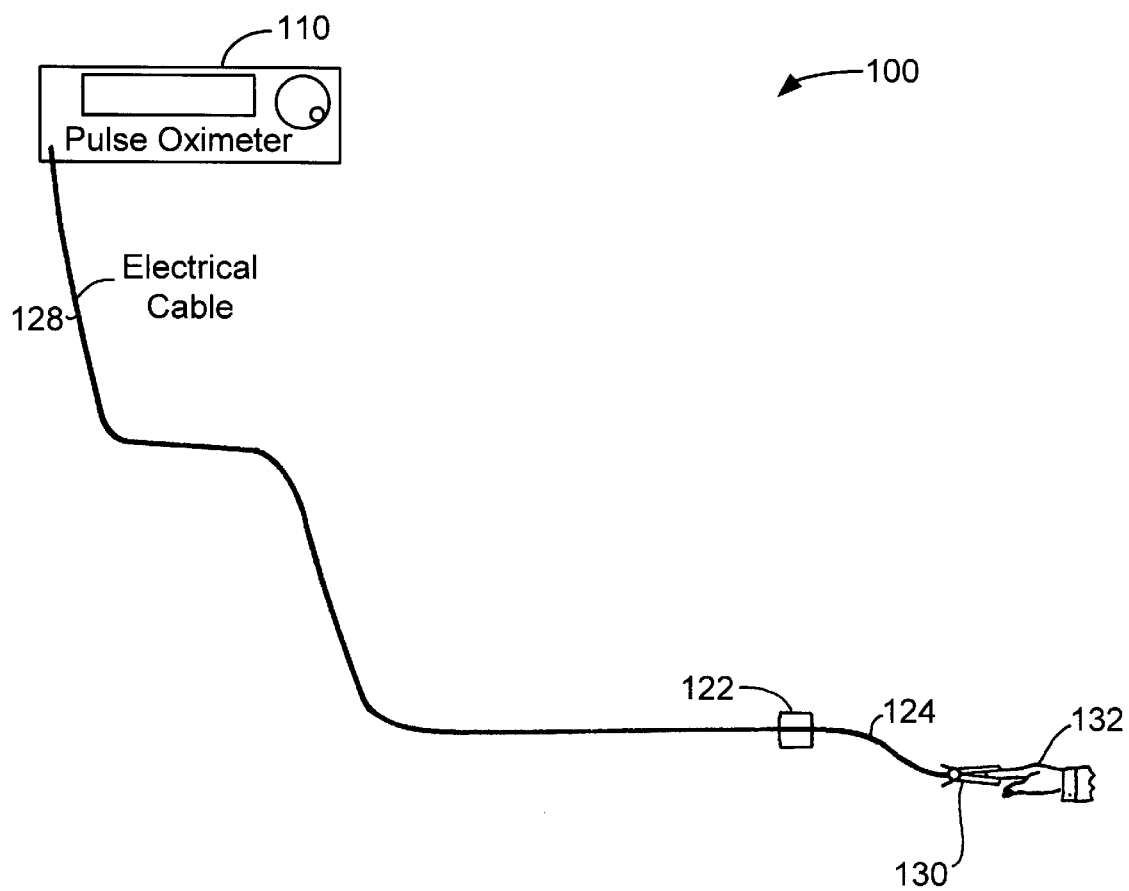
FIG. 1 shows a simplified block diagram of an embodiment of an oxygen measurement system.

FIG. 1 shows a simplified block diagram of an embodiment of a physiological measurement system 100. System 100 includes a monitor 110. Monitor 110 couples via an electrical cable 128 to a sensor 130 that is applied to a patient 132. Sensor 130 includes a sensor cable 124 and a sensor connecting plug 122. Sensor 130 optionally includes light sources (e.g., LEDs) and a photo-detector along with suitable components to couple the electro-optical components to electrical cable 128. Sensor 130 is shown in FIG. 1 as a clip-on sensor. However, the invention can be applied to many sensor implementations, including those attached to a patient by adhesive and other attachment means. In a specific embodiment, monitor 110 is a pulse oximeter and sensor 130 is a pulse oximeter sensor. However, the sensor could alternatively be a temperature, heart rate, blood pressure, or other type of physiological sensor.

For a preferred embodiment, for estimating blood oxygen saturation, light from light sources at two or more wavelengths (e.g., red and infrared) is transmitted through a patient's blood perfused tissues (e.g., in a finger) and detected by a photo-detector. The selection of the wavelengths is based on a number of factors. Such factors include the absorption characteristics of the patient and transmission medium. The light sources and photo-detector are typically housed within a sensor that couples to the monitor (e.g., the pulse oximeter). The detected optical signal is then provided to the monitor for processing.

Figure 2:
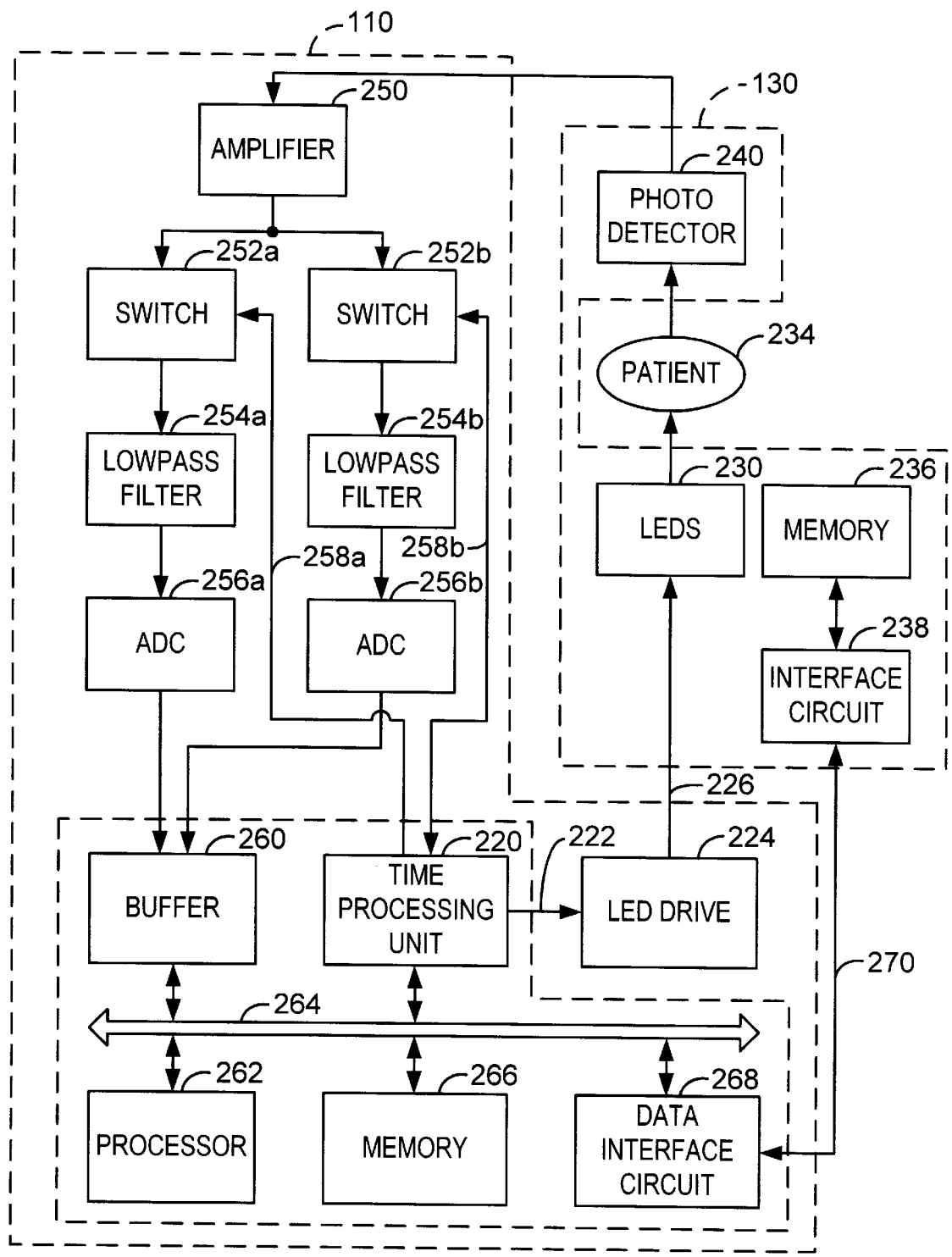
FIG. 2 shows a block diagram of an embodiment of an oxygen monitor and sensor.

FIG. 2 shows a block diagram of an embodiment of monitor 110 and sensor 130. Within monitor 110, a time processing unit (TPU) 220 provides control signals 222 to an LED driver 224 that, via data line(s) 226, alternately activates LEDs 230 within sensor 130. Depending on the particular implementation, LEDs 230 include two or more LEDs and LED driver 224 provides the necessary drive signals for the LEDs. When activated, the light from LEDs 230 passes through a medium (e.g., air or a fiber optic cable, depending on the implementation) into a patient's tissues 234. After being transmitted through or reflected from the tissues, the light is received by a photo-detector 240 via another medium (e.g., air or another fiber optic cable). Photo-detector 240 converts the received light into a photo-current, which is then provided to an amplifier 250 that amplifies the photo-current.

As shown in FIG. 2, the amplified signal from amplifier 250 is provided to circuitry for two different channels, one channel for each of the red and infrared wavelengths. For a three-wavelength implementation, circuitry is provided for three channels. Each channel circuitry includes an analog switch 252 coupled in series with a low pass filter 254 that is further coupled in series with an analog-to-digital converter (ADC) 256. Control lines 258 from time processing unit 220 select the sampled data from the channel corresponding to the LED being activated. Specifically, the sampled data from ADC 256a is selected when the red LED is activated and the sampled data from ADC 256b is selected when the infrared LED is activated. The sampled data from ADCs 256 is provided to a buffer 260 that stores the data for further processing. In an implementation, as buffer 260 periodically fills up, a processor 262 coupled to a bus 264 directs the transfer of the data from buffer 260 into a memory 266. The monitor implementation shown in FIG. 2 is one of many implementations. Another pulse oximeter implementation is disclosed in the aforementioned U.S. Pat. No. 5,853,364. The present invention can be adapted for application in various monitor implementations.

The sensor of the invention further includes circuitry that stores historical physiological data and provides the data when requested. As shown in FIG. 2, sensor 130 includes a memory 236 coupled to an interface circuit 238. Interface circuit 238 provides signal conditioning, and can also provide other functions such as address decoding, and so on. Interface circuit 238 couples via a bus 270 to a data interface circuit 268 within monitor 110. Through interface circuits 238 and 268, physiological data is transferred between monitor 110 and sensor 130.

In an embodiment, to enhance compatibility of the sensor of the invention with conventional sensors and conventional monitors, bus 270 is implemented using new signal lines (i.e., not using or sharing the existing signal lines of conventional sensors). Bus 270 can be implemented as a serial bus, a parallel bus, or other bus architectures. With this implementation, when sensor 130 of the invention is plugged into a monitor not capable of supporting the features of the invention, the signals on interface circuit 238 are simply ignored by the monitor, or alternatively not be requested by the monitor.

In another embodiment, interface circuits 238 and 268 interact via signal line(s) or wire(s) existing in conventional sensors and monitors. For example, interface circuits 238 and 268 can couple via data line(s) 226 and time multiplex with the LED drive signals from LED driver 224.

Time processing unit 220, buffer 260, processor 262, memory 266, and data interface circuit 268 can be implemented in various manners. For example, these elements can be implemented within a single integrated circuit, such as a DMC68HC16 micro-controller from Motorola. These elements can also be implemented within an application specific integrated circuit (ASIC), a digital signal processor, a micro-controller, or other circuits.

Memory 236 can be implemented as a write once memory, a random access memory (RAM), a FLASH memory, a programmable read only memory (PROM), an erasable PROM (EPROM), an electrically erasable PROM (EEPROM), or other memory technologies capable of write and read operations. Memory 236 and interface circuit 238 can be integrated within one integrated circuit for reduced size and cost.

In a specific embodiment, to preserve the historical data and prevent accidental erasure, the sensor memory can be written only once. This memory characteristic also prevents erasure of the data during sensor operation. A specific example of a memory device that can be written only once is a 2-wire EPROM device available from Dallas Semiconductor Corp.

In another embodiment, the memory can be erased and overwritten multiple times. This memory characteristic may be advantageous, for example, for non-disposable sensors that may be used multiple times on multiple patients. Specific examples of memory devices that can be erased and overwritten are Flash, EEPROM, battery backed RAM, and other technologies.

The memory 236 associated with the sensor can be physically located in a variety of places. First, it can be located on the body of the sensor, in a vicinity of the photodetector, LEDs, or other sensor components. Or, the memory can be in the sensor connecting cable 124 or the sensor connecting plug 122, or in an adapter module that connects to a front of an oximeter, to an oximeter cable, or to a sensor plug or cable. Whether or not the memory 236 is in the sensor body, sensor cable 124, sensor plug 122, or adapter module, it is always "associated with" the sensor since the memory travels with the sensor and patient when the patient is moved and the sensor is disconnected from the monitor.

During normal operation, when the sensor is plugged into the monitor, the monitor receives the signal from the photodetector within the sensor and processes this signal to obtain the desired physiological data. In some prior art conventional monitors, the physiological data is stored in a memory within the monitor and retrieved at a later time by a caregiver when requested. However, when a patient is moved to new locations and different monitors are used, the data stored in the monitor at the previous site is typically not available at the current site, and the historical data is unavailable.

In accordance with the invention, the physiological data is processed, displayed, and stored in the monitor in the normal or usual manner. In addition, the data is compressed and provided to the sensor for storage in the memory 236 associated with the sensor. Alternatively, uncompressed data can be provided to and stored in the memory 236. When the sensor is later plugged into another monitor, the new monitor can retrieve the data stored in the sensor memory, decompress the retrieved data, and display the decompressed data. In an embodiment, when the sensor is first plugged into a new monitor, the monitor retrieves and displays the historical physiological data for the most recent predetermined period (i.e., the last 20 or 30 minutes). This predetermined period can be programmed by the clinician or can be preprogrammed into the sensor memory.

Alternatively, the monitor can be configured to retrieve and display the historical physiological data at any time upon request by a health care giver (or a clinician), by the health care giver simply activating a control knob on the monitor. The monitor optionally can be preset so as to automatically retrieve the data upon occurrence of a predetermined event, such as a sensor being plugged into the monitor, or can by preconfigured so that the data is only retrieved upon explicit command by a health care giver.

The monitor and sensor can be configured such that the data is provided to and stored in the memory 236 automatically and continuously. The monitor and sensor also employ automated event recording, such that the monitor in response to an oxygen desaturation event transfers some of the physiological data to the sensor memory. Alternatively, particularly when a size of the memory is small, the monitor can require a user first command the monitor (e.g., by activating a control knob) to send data to the memory 236. In this case, valuable storage space in the memory 236 will only be used (and consumed) when the patient being monitored is believed to be relatively unstable by the caregiver and when it is believed storage of the historical data for later retrieval may be particularly desirable.

As noted above, the invention can be used to store and provide various physiological data including, but not limited to, blood oxygen saturation, heart rate, temperature, and blood pressure data. For clarity, the invention is described in the context of the storage and retrieval of blood oxygen saturation ($SpO_2$) data. Based on the received signals representative of the intensity of the light detected by photodetector 240, processor 262 estimates oxygen saturation using algorithms that are known in the art.

The saturation data for a particular patient is processed by the monitor attached to the sensor, and the processed data is provided to the sensor for storage in the sensor memory. The selection of the sensor memory is dependent on numerous factors including cost, the amount of data that needs to be stored for a particular application, the amount of achievable data compression (if compression is used), the physical dimensions, and so on. For oxygen saturation, storage of approximately one to seven days of historical data is adequate for many applications.

In an embodiment, to reduce the amount of data to be stored in the sensor memory, the physiological data is compressed before storage. In an embodiment, the compression is performed by facilities located within the monitor. Alternatively, the compression encoding circuit can be on the sensor itself. The monitor further includes facilities to decompress the data later retrieved from the sensor memory. Compression allows for the use of a smaller-sized memory in the sensor. This is particularly advantageous in the case of single patient use disposable sensors which are typically disposed after use on a patient. Compression also allows more data to be stored into a memory of a given size. The ability to store a large amount of data is important for many diagnostic applications that require data collected over hours or days.

The compression scheme can be designed to take advantage of known characteristics of the physiological data being stored. For example, it is known that oxygen saturation generally does not change rapidly. This characteristic can be exploited to achieve significant compression, as described below.

For arterial oxygen saturation data, one preferred compression scheme is based on the realization that saturation data generally exists in two dimensions, time and absolute saturation value. Saturation sample time is about one hertz normally, assuming one saturation value is determined by a monitor for each patient heartbeat. The number of possible saturation values generally corresponds to 101 possibilities, which assumes each possibility corresponds to an integer saturation percentage which must lie somewhere between 0% to 100%. A preferred goal is to use a compression coding technique which reduces the scope of these two dimensions, which again are 1 Hz by 101 saturation values, to a smaller region, e.g., 0.1 Hz by 8 saturation values, for example, and yet retain the usefulness of the information. According to a preferred embodiment, Huffman compression is used with run length encoding, or alternatively or additionally differential encoding.

Run length encoding simply means that if the same saturation value is to be repetitively transmitted, rather than repetitively transmitting this value, it can be more efficient to count the number of consecutive times the value occurs, and to instead transmit the value and the number of times it is repeated. Differential encoding, though similar, is different in that a difference between consecutive saturation values to be transmitted is calculated, and along with the original saturation value one transmits the differential between adjacent values and the number of times an identical differential occurs. There are many known permutations of these two types of common compression techniques known in the art.

As noted above, if saturation percentages were to be reduced to a group of eight values, any single value would correspond to a range of saturation percentages. For example, ten values could be selected, with each value corresponding to an incremental increase of 10 saturation percentage points. A disadvantage of such a grouping is that a patient who has a saturation which is toggling between groups by only one saturation percentage, e.g., toggling between 89% and 90%, can require a great deal of memory to record this information since the advantages of run length encoding are greatly diminished if the identity of the group is repetitively changing.

Accordingly, it has been determined that it is preferred to utilize saturation values which have saturation percentages which overlap. For example, eight saturation values could be as follows:

| Saturation Value # | Saturation Range (%) |
|---|---|
| 1 | 85–100 |
| 2 | 80–90 |
| 3 | 75–84 |
| 4 | 70–79 |
| 5 | 65–74 |
| 6 | 60–69 |
| 7 | 1–64 |
| 8 | 0 |

Since these saturation values have saturation percentages which overlap, toggling at a boundary between values 1 and 2 is prevented for small saturation changes. For example, if value 2 has previously been stored based on a saturation of 90%, and the saturation moves to 91%, the saturation range will now correspond to value 1, and this value will be maintained until the patient saturation falls below 85%. Hence, with overlapping values or groups, it is readily apparent the advantages of run length encoding will be more readily achieved for all patients except the most unstable whose saturation varies by relatively large amounts in relatively short periods of time.

Turning to the other dimension involved with saturation, specifically saturation sampling frequency, for a sampling rate of 0.1 Hz, a single saturation value can be determined for a patient based upon their average saturation every 10 seconds. Lower sampling frequencies could be used which generate less data, which consume less memory, but a disadvantage is that correspondingly less information will be stored in the memory. Conversely, higher sampling frequencies could be used which result in more information being stored in the memory, with a corresponding disadvantage that more memory is required.

Regardless of the saturation sampling frequency, and the number of saturation values or groups which are used, further compression can be achieved by overlaying Huffman encoding techniques, which simply means that if a mean value to be transmitted is relatively high, such as 95, this value can be normalized to 0 using Huffman encoding techniques with the result that fewer bits are required to transmit relatively large numbers by such normalization.

Several compression embodiments have been described for oxygen saturation data. Although the invention can be practiced without the use of compression, additional capabilities are provided by the judicious use of compression. As used herein, compression includes any processing that alters, however slightly, the original form of the physiological data as they are generated (in the nominal manner) by the monitor. Other compression schemes can also be used and are within the scope of the invention. Of course, no compression could optionally be used.

Additional data besides oxygen saturation data can be stored in the sensor memory (i.e., to assist in diagnostics or monitoring of patients). For example, a time stamp of the data can be stored. In this case, the first data sample includes the specific time (e.g., date and time) when the data is recorded. Subsequent data samples can be indicated by the number of epochs away from the first (or a previous) data sample. The sensor memory can also store an indication of a disconnection of the sensor from the monitor. This data allows the clinician or medical personnel to delineate the events retrieved from the sensor memory.

The sensor memory can also include a field that indicates when the sensor memory is full. The information in this field can be provided to the monitor to direct the monitor to cease sending data to the sensor memory. The information in this field can be prominently displayed by the monitor to notify the clinician or medical personnel. Also, in response, the monitor can generate an alarm (i.e., blinking light or an audio alarm, or both) to draw the attention of the clinician to the operating state of the sensor.

As noted above, in a specific embodiment, the sensor memory is implemented as a write-once memory device. A field in the sensor memory can be set when the sensor is reprocessed so that the monitor can determine that it is coupled to a reprocessed sensor. The monitor can use the information in this field to disable the display of the historical data (for example, if the memory is write once and relatively full). Alternatively, if the memory is erasable, a field for storing historical physiological data could be erased during sensor reprocessing.

Disabling the data display may be preferable in some applications to ensure the integrity of the collected data. For a memory device that can be written once and has a fixed memory size, it may not be possible to determine where the "old" data came from or how much memory may still be available on a reprocessed sensor. Moreover, it is highly desirable to avoid having data from an old patient being displayed and potentially mistaken as valid data for the patient to which the sensor couples. Since it is not easy to control or determine the amount of available unwritten memory after a use, which can vary from zero to the full amount, inconsistency and potential customer dissatisfaction may result from using a sensor having widely varying amounts of available memory. By not displaying data from reprocessed sensors, these potential problems are avoided.

The invention has been described for the storage of blood oxygen saturation data. However, the sensor memory can also store data for other physiological characteristics such as, for example, heart rate, blood pressure, temperature, and so on. For example, the sensor memory can be used to store NIBP, IBP, and ECG waveforms. Moreover, as memory costs continue to fall and larger memories become available, more complex physiological parameters can be measured and stored.

Additionally, information about the monitor can be stored or embedded along with the physiological data. This additional information may include, for example, the serial number of the monitor to which the sensor couples, the sensor connect/disconnect times, monitor diagnostics, and others. This information would allow the clinician to access historical information on the instrument as well as the physiological data, which might be useful, for example, in product liability and malpractice litigation or in troubleshooting instrument performance questions.

The invention provides advantages not available in conventional monitors and sensors. For example, the invention allows for monitoring of a patient in transit who may be connected to two or more monitors over a period of time. One such situation is a patient who is transported in an ambulance to an emergency room and later transferred to, an intensive care unit. The invention is especially beneficial in this application since this particular patient is more likely to be in need of close monitoring and recent historical physiological information.

The invention can also be used to document physiological characteristics. For example, for a patient in home care who requires oxygen, documentation of oxygen saturation is typically needed. In this case, the sensor of the invention can be used to store saturation data for the patient over a predetermined time period (i.e., one week). At the end of this period, the caregiver can simply remove the sensor and send it away as documentation of the patient's saturation. The invention can also be used to collect data for other applications such as, for example, sleep diagnostics, de-saturation, and so on.

The sensor of the invention has been described for use in combination with a monitor that performs the signal processing of the detected signal and compression of the processed data. In another embodiment, the sensor of the invention includes the facility to process (and compress, if necessary or desirable) the detected signal. This embodiment advantageously allows for independent operation of the sensor without support from a monitor. The data stored within the sensor can be provided to a monitor for display. The amount of signal processing and compression that can be achieved by circuitry within the sensor is only limited by the available technology, which inevitably improves over time. In the near term, physiological data that does not require extensive signal processing and compression (e.g., temperature, peak amplitude in a waveform, heart rate, and so on) can be collected and stored by the sensor.

The previous description of the preferred embodiments is provided to enable any person skilled in the art to make or use the present invention. Various modifications to these embodiments will be readily apparent to those skilled in the art, and the generic principles defined herein may be applied to other embodiments without the use of inventive faculty. For example, the invention can be applied to the storage of other physiological data, such as data for a patient's heart rate, temperature, volume of individual blood pulsation supplying the tissue, and so on. Thus, the present invention is not intended to be limited to the embodiments shown herein but is to be accorded the widest scope consistent with the principles and novel features disclosed herein.

What is claimed is:

1. A physiological sensor for connecting to a first monitor, comprising:
   means for obtaining signals from a patient indicative of a physiological condition of the patient;
   means for sending the signals to said first monitor; and
   a sensor memory circuit associated with said physiological sensor and located outside any monitor which processes said signals, said sensor memory stores patient physiological data derived from the signals by said first monitor and which are indicative of the physiological condition, the sensor memory circuit providing the data to any monitor when requested by said any monitor, such that when said sensor is disconnected from said any monitor said sensor memory is physically connected with and moves with said sensor.

2. The sensor of claim 1, wherein said monitor comprises a second any monitor.

3. The sensor of claim 1 wherein said memory circuit is implemented as a write-once memory, a FLASH memory, a random access memory (RAM), an erasable memory, or an electrically erasable programmable read only memory (EEPROM).

4. The sensor of claim 1 wherein said physiological data includes arterial blood oxygen saturation data.

5. The sensor of claim 1 wherein said physiological data is compressed before storage to the memory circuit.

6. The senor of claim 5 wherein said physiological data is compressed using one of the following: differential coding, runlength coding, or Huffman encoding.

7. The sensor of claim 6 wherein said physiological data is subsampled to provide one data sample for each epoch, wherein an epoch is a predetermined time period selected, in part, based on characteristics of physiological data being stored, a quantity of each data sample being fixed for a range of physiological data values, the data samples being packetized before being transmitted to the memory circuit.

8. The sensor of claim 1 wherein said physiological data is uncompressed when stored on said memory circuit.

9. The sensor of claim 1 wherein said memory circuit provides information to said first monitor that indicates when the memory circuit is full.

10. The sensor of claim 1 wherein said memory circuit further stores information of a time associated with each of specific samples of the physiological data.

11. A method for storing physiological data comprising:
   detecting via a sensor at least one signal indicative of a physiological condition;
   conditioning the detected at least one signal to generate data samples;
   processing the data samples to generate the physiological data, wherein said physiological data describes the physiological condition; and
   storing the physiological data within a sensor memory associated with said sensor and located outside a monitor which processes the data samples, such that when said sensor is disconnected from said monitor said sensor memory is physically connected with and moves with said sensor.

12. The method of claim 11 wherein said physiological data includes blood oxygen saturation data.

13. A physiological monitoring instrument comprising:
   a first monitor including
      conditioning circuitry that receives an electrical signal and processes the electrical signal to provide sampled data, and
      processing circuitry that processes the sampled data to provide physiological data, wherein the physiological data is indicative of a physiological condition of a patient; and
   a sensor coupled to the first monitor, said sensor having a sensor memory circuit, said sensor memory circuit configured to store at least some of the physiological data from said first monitor and provide the data when requested, wherein said memory circuit is located outside any monitor which processes said signals, such that when said sensor is disconnected from said any monitor said sensor memory is physically connected with and moves with said sensor.

14. The physiological monitoring instrument of claim 13 wherein said first monitor further includes means responsive to a user input for transferring at least some of said physiological data to said memory circuit in response to user input.

15. The physiological monitoring instrument of claim 13 wherein the first monitor further includes means responsive to an oxygen desaturation event for transferring at least some of said physiological data to said memory circuit in response to the oxygen desaturation event of the patient.

16. The physiological monitoring instrument of claim 13 wherein said first monitor further includes means responsive to a threshold crossing for transferring at least some of said physiological data to said memory circuit when an oxygen saturation of the patient differs by more than a predetermined amount from a previous oxygen saturation of the patient.

17. The physiological monitoring instrument of claim 13 wherein said first monitor further includes an encoder coupled to said processing circuitry, wherein said encoder codes said physiological data to provide compressed physiological data for transmission to said sensor memory circuit.

18. The physiological monitoring instrument of claim 17 wherein said first monitor further includes a decoder that receives compressed physiological data from said memory circuit and decodes said data.

19. The physiological monitoring instrument of claim 13 wherein said physiological data includes blood oxygen saturation data.

20. An oximeter system for storing and providing historical saturation data of a patient comprising:

two or more light sources for transmitting light through the patient, wherein said light sources operate at different wavelengths;

a detector that detects optical signals from said light sources and provides electrical signals indicative of the detected optical signals;

conditioning circuitry that processes said electrical signals to provide data samples corresponding to the electrical signals;

processing circuit that receives said data samples and processes said data samples to provide saturation data;

a sensor memory connected with a sensor that stores said saturation data, wherein said sensor memory is located outside a monitor which processes said electrical signals, such that when said sensor is disconnected from said monitor said sensor memory is physically connected with and moves with said sensor; and circuitry that retrieves the stored saturation data and directs display of said saturation data.

* * * * *